United States Patent
Richard et al.

(10) Patent No.: US 6,517,742 B1
(45) Date of Patent: *Feb. 11, 2003

(54) SUNSCREEN AGENTS, PHOTOPROTECTIVE COSMETIC COMPOSITIONS CONTAINING THEM AND USES THEREOF

(75) Inventors: Hervé Richard, Villepinte (FR); Madeleine Leduc, Paris (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/965,538

(22) Filed: Nov. 6, 1997

(30) Foreign Application Priority Data

Nov. 8, 1996 (FR) .............................. 96 13684

(51) Int. Cl.⁷ ............................... C09K 15/16
(52) U.S. Cl. ................. 252/401; 544/196; 544/197; 544/198; 544/199; 514/241; 514/880; 514/881; 424/70.1; 424/70.9; 424/60; 424/401; 524/100
(58) Field of Search ................ 544/196, 197, 544/198, 199; 514/241, 880, 881; 424/70.1, 70.9; 524/100

(56) References Cited

U.S. PATENT DOCUMENTS

| 2,949,434 | A | * | 8/1960 | Bailey et al. ........... 544/196 |
| 3,546,223 | A | * | 12/1970 | Senge et al. ........... 260/249.6 |
| 4,136,092 | A | * | 1/1979 | Jackle et al. ........... 544/197 |
| 4,609,404 | A |   | 9/1986 | Maraccini et al. ...... 106/288 |
| 5,236,698 | A | * | 8/1993 | Richard et al. ......... 544/197 |
| 5,849,909 | A |   | 12/1998 | Richard et al. ......... 544/216 |
| 5,955,060 | A |   | 9/1999 | Hüglin et al. .......... 544/216 |

FOREIGN PATENT DOCUMENTS

| EP | 507 691 | 10/1992 |
| EP | 517 104 | 12/1992 |
| EP | 775 698 | 5/1997 |
| JP | 59-49261 | 3/1984 |
| JP | 5-230040 | 9/1993 |
| JP | 9-188666 | 7/1997 |
| JP | 9-227533 | 9/1997 |

OTHER PUBLICATIONS

Ford et al. J. Phys. Chem. 98(14), 3822–31, 1994. CAPLUS abstract provided.*
NIST UV Data—Aniline.*
NIST UV Data—p–aminobenzoic acid.*
NIST UV Data—1,3–butadiene.*

* cited by examiner

Primary Examiner—Richard L. Raymond
Assistant Examiner—Venkataraman Balasubramanian
(74) Attorney, Agent, or Firm—Finnegan, Henderson, Farabow, Garrett & Dunner, L.L.P.

(57) ABSTRACT

The invention relates to new s-triazine derivatives of the formula (I):

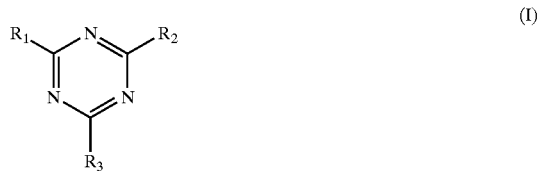

in which $R_1$ represents an —NH—F radical, wherein F is a screening chromophore; $R_2$ represents an —NH—Z—W radical, wherein Z is a divalent radical providing the connection between —NH— and —W, and W is a silicone-containing radical; and $R_3$ is $R_1$, $R_2$, a linear or branched $C_1$–$C_{20}$ alkyl radical, a linear or branched $C_2$–$C_{20}$ hydroxyalkyl radical, a linear or branched $C_1$–$C_{20}$ alkoxy radical, an $NHR_8$ radical or an $N(R_8)_2$ radical, with $R_8$ being a linear or branched $C_1$–$C_{20}$ alkyl radical. The compounds of the invention are useful as organic sunscreen agents in cosmetic compositions intended for the protection of the skin and the hair against ultraviolet radiation. The invention also relates to the use of the compounds in cosmetic applications and to cosmetic compositions with improved properties containing these compounds.

21 Claims, No Drawings

SUNSCREEN AGENTS, PHOTOPROTECTIVE COSMETIC COMPOSITIONS CONTAINING THEM AND USES THEREOF

The invention relates to new s-triazine derivatives substituted by at least one silicone group and at least one aminobenzylidenecamphor, aminobenzalmalonate, aminobenzoate, or alternatively aminobenzotriazole, aminobenzimidazole, aminobenzoxazole, aminobenzothiazole, aminosalicylate, aminocinnamate and/or aminocinnamonitrile group; these compounds being more particularly employable as organic sunscreen agents in cosmetic compositions intended for protecting the skin and hair against ultraviolet radiation. The invention also relates to the use of these compounds in the above-mentioned cosmetic applications, and to the cosmetic compositions with improved properties containing them.

It is known that light radiation with wavelengths of from 280 nm to 400 nm makes possible tanning of the human epidermis and that rays with wavelengths more particularly of from 280 to 320 nm, known under the name UV-B, cause skin burns and erythemas which may be harmful to the development of a natural tan. For these reasons, and for aesthetic reasons, there is a constant demand for means of controlling this natural tanning with a view to thus controlling the color of the skin; it is therefore advisable to screen out this UV-B radiation.

It is also known that UV-A rays, with wavelengths of from 320 to 400 nm, which cause tanning of the skin, are liable to induce an adverse, change in the latter, especially in the case of sensitive skin or of skin which is continually exposed to solar radiation. UV-A rays cause in particular a loss of elasticity of the skin and the appearance of wrinkles, leading to premature skin aging. They promote triggering of the erythemal reaction or amplify this reaction in certain individuals and may even be the cause of phototoxic or photoallergic reactions. Thus, for aesthetic and cosmetic reasons, such as retaining the natural elasticity of he skin, for example, increasing numbers of people wish to control the effect of UV-A rays on their skin. It is thus desirable also to screen out UV-A radiation.

Many compounds intended for the photoprotection (UV-A and/or UV-B) of the skin have been provided to date.

Most of them are aromatic compounds exhibiting absorption of UV rays in the region from 280 to 315 nm or in the region from 315 to 400 nm or alternatively in both of these two regions. They are most often formulated in anti-sun compositions which are provided in the form of an emulsion of oil-in-water type (that is to say a cosmetically acceptable vehicle composed of a continuous aqueous dispersing phase and of a non-continuous oily dispersed phase) and which thus contain, at various concentrations, one or more conventional lipophilic and/or hydrophilic organic screening agents with an aromatic functional group which are capable of selectively absorbing harmful UV radiation, these screening agents (and their amounts) being selected as a function of the desired sun protection factor (the sun protection factor being expressed mathematically by the ratio of the irradiation time necessary to reach the erythemogenic threshold with the UV screening agent to the time necessary to reach the erythemogenic threshold without UV screening agent).

In addition to their screening power, these compounds with an anti-UV activity must also exhibit good cosmetic properties in the compositions which contain them, good solubility in the usual solvents, and in particular fatty substances such as oils and fats, and good resistance to water and to perspiration (persistence).

Among all the aromatic compounds which have been recommended for this purpose, mention may in particular be made of derivatives of p-aminobenzoic acid, derivatives of benzylidenecamphor, derivatives of cinnamic acid and derivatives of benzalmalonate. However, some of these substances do not exhibit all the properties required for suitable use as UV screening agents in anti-sun compositions. In particular, their intrinsic screening power may be insufficient, their solubility in the various types of formulations used for sun projection is not always sufficiently good (in particular liposolubility), they may not possess sufficient stability to light (photostability). and they may also exhibit poor resistance to water and to sweat. It is also desirable for these screening substances not to penetrate into the skin.

Thus, in the more specific case of screening substances of benzalmalonate, benzotriazole or benzylidenecamphor type, attempts have been made to obtain products with improved properties, in particular with respect to their liposolubility and their screening power,, by attaching, by grafting, one or more screening benzylidenecamphor, benzotriazole or benzalmalonate groups to an s-triazine. This technique, described in Patent Applications EP 0,507,691 and EP 0,507,692, certainly results in advantageous compounds but the liposoluble nature of the latter may still appear to be insufficient and, moreover, in order to obtain satisfactory screening properties with this type of product, it is often necessary to employ relatively large amounts of these screening agents, which is reflected by poor cosmetic properties with respect to the formulations which contain them.

Likewise, in the documents EP 0,517,104 and U.S. Pat. No. 4,724,137, attempts have been made to increase the SPF of derivatives of p-aminobenzoic acid by grafting three p-aminobenzoate groups onto an s-triazine. Compounds exhibiting a good SPF but with very low liposolubility are obtained. The formulation of such compounds proves to be difficult and tedious and requires the addition of solubilizing substances, sometimes in large amounts.

The aim of the present invention is to solve the above problems by providing new compounds, of silane or siloxane s-triazine type, with an aminobenzylidenecamphor, aminobenzalmalonate, aminobenzoate, or alternatively aminobenzotriazole,,aminobenzimidazole, aminobenzoxazole, aminobenzothiazole, aminosalicylate, aminocinnamate and/or aminocinnamonitrile functional group, which exhibit improved properties, in particular with respect to their solubility in fatty substances and their intrinsic absorption power with respect to UV radiation.

More specifically still, it has been found, according to the present invention, that, by grafting onto an s-triazine, on the one hand, at least one specific silicone chain or one specific silane and, on the other hand, one or more screening chromophores, it is possible to produce new compounds which overcome the disadvantages of the screening agents of the prior art, these new compounds exhibiting, in addition to very high screening properties, very good solubility in the usual organic solvents, in particular fatty substances such as oils, and excellent cosmetic properties, making them particularly suitable for use as sunscreen agents in, or for the preparation of, cosmetic compositions intended for the protection of the skin and/or hair against ultraviolet radiation.

Screening chromophore is understood to mean, within the meaning of the present invention, a group which absorbs UV radiation in the region from 280 nm to 400 nm. Screening chromophores which are particularly well suited to the preparation of the compounds according to the invention are derivatives of aminobenzylidenecamphor, aminobenzalmalonate, aminobenzoate, aminobenzotriazole, aminobenzimidazole, aminobenzoxazole, aminobenzothiazole, aminosalicylate, aminocinnamate, and/or aminocinnamonitrile.

The first subject of the present invention is thus new compounds which are characterized in that they correspond to the following general formula (I):

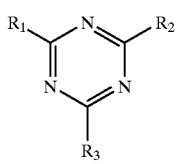
(I)

in which:

$R_1$ represents an —NH—F radical, $R_2$ represents an —NH—Z—W radical, $R_3$ is $R_1$, $R_2$, a linear or branched $C_1$–$C_{20}$ alkyl radical, a linear or branched $C_2$–$C_{20}$ hydroxyalkyl radical, a linear or branched $C_1$–$C_{20}$ alkoxy radical, the $NHR_8$ radical or the $N(R_8)_2$ radical, with $R^8$ independently being a linear or branched $C_1$–$C_{20}$ alkyl radical F represents a screening chromophore, Z represents a divalent radical providing the connection between —NH— and —W, W represents either a silicone radical comprising at least one unit of following formula (1):

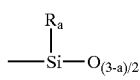
(1)

in which R denotes a saturated or unsaturated $C_1$–$C_{30}$ hydrocarbon group, a halogenated $C_1$–$C_8$ hydrocarbon group or a trimethylsilyloxy group and a is 1 or 2, or a radical of following formula (2):

(2)

in which $R'_1$, $R'_2$ and $R'_3$, which are identical or different, are selected from linear or branched $C_1$–$C_8$ alkyl and alkenyl radicals.

Preferably, the screening chromophore F is selected independently from derivatives of benzylidenecamphor, of benzalmalonate, of benzoate or alternatively of benzotriazole, of benzimidazole, of benzoxazole, of benzothiazole, of salicylate, of cinnamate and/or of cinnamonitrile. This chromophore F is more preferably still selected independently from the radicals of following formulae A to E:

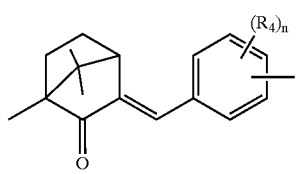
A

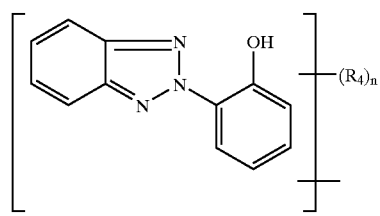
B

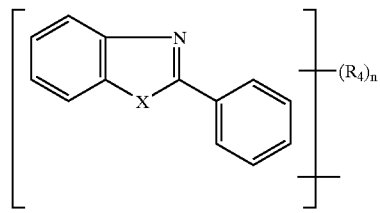
C

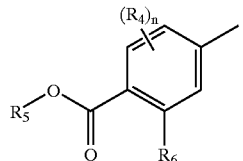
D

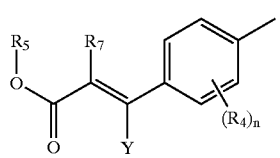
E in which:

$R_4$, which are identical or different, denote a linear or branched $C_1$–$C_8$ alkyl radical or a $C_1$–$C_4$ alkoxy radical, it being possible for two adjacent $R_4$ groups on the same aromatic nucleus together to form an alkylidenedioxy group, in which the alkylidene group contains 1 or 2 carbon atoms, n is 0, 1 or 2, $R_5$ is a linear or branched $C_1$–$C_{20}$ alkyl radical, $R_6$ represents a hydrogen atom, a hydroxyl radical or a $C_1$–$C_6$ alkoxy radical, $R_7$ represents a hydrogen atom, $COOR_5$ or the cyano radical, X is an oxygen or sulphur atom or the N—$R_9$ group, with $R_9$ being a hydrogen atom or a linear or branched $C_1$–$C_4$ alkyl radical, Y represents a hydrogen atom or a phenyl radical optionally substituted by a $C_1$–$C_4$ alkyl or alkoxy radical.

The divalent radical Z is preferably selected from the radicals of the following formulae (a) or (b):

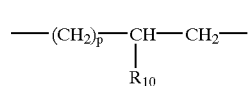
(a)

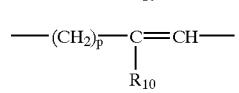
(b)

in which $R_{10}$ represents a hydrogen atom or a saturated or unsaturated, linear or branched $C_1$–$C_8$ alkyl radical and p is an integer from 0 to 10.

In a preferred form of the invention, W is a silicone radical corresponding to one of the three following formulae (3) to (5):

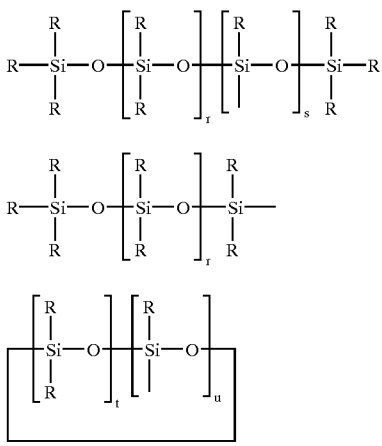

in which:

R, which are identical or different, are selected from saturated or unsaturated, linear or branched $C_1$–$C_{10}$ alkyl radicals, a phenyl radical and a 3,3,3-trifluoropropyl radical, at least 80% by number of the R radicals being the methyl radical, r is an integer from 0 to 50 inclusive, s is an integer from 0 to 20 inclusive, u is an integer from 1 to 6 inclusive, t is an integer from 0 to 10 inclusive, t+u is equal to or greater than 3.

The compounds of the invention exhibit excellent liposolubility and can thus be used at high concentrations, which confers very high protection factors on the final compositions; moreover, they. are distributed uniformly in conventional cosmetic vehicles containing at least one cosmetically acceptable organic solvent or fatty phase and can thus be applied to the skin or hair in order to constitute an effective protective film. Moreover, their cosmetic properties are very good: in particular, these products contribute softness.

In addition, the compounds of the invention exhibit an excellent intrinsic screening power with respect to UV-A and/or UV-B ultraviolet radiation, depending on the structure of the product. In fact, depending on the nature of the $R_1$ and $R_3$ groups, a final compound will be obtained which absorbs more particularly in the UV-A or, in contrast, more particularly in the UV-B. Thus, if it is desired to obtain a compound which absorbs more particularly in the UV-A, it will be advantageous to graft, onto the triazine, one or more groups selected from the aminobenzylidenecamphor, aminobenzoxazole and aminobenzalmalonate derivatives or certain aminobenzotriazole derivatives (radicals A, C and E and certain radicals B above). In contrast, if it is desired to obtain a compound which absorbs more particularly in the UV-B, it will be advantageous to graft, onto the triazine, one or more groups selected from aminobenzoate derivatives or certain aminobenzotriazole derivatives (certain radicals B and radicals D above). One of the great advantages of the present invention is thus to provide UV screening agents which absorb in all UV radiation (namely in the wavelength range from 280 nm to 400 nm), these screening agents being obtained by grafting, onto the same triazine, both a group exhibiting high absorption in the UV-A and a group exhibiting absorption in the UV-B (for example, a compound in which $R_1$ is an —NH—A radical and $R_3$ is an —NH—D radical).

By virtue of the present invention, it is thus possible to have available a composition which, taken as a whole, will exhibit an exceptional screening activity throughout the range of harmful UV radiation (UV-A+UV-B), either by using at least one compound of the invention exhibiting two different groups, one absorbing in the UV-A and the other absorbing in the UV-B, or by mixing products of different structure, that is to say more specifically by mixing products in accordance with the invention exhibiting a purely UV-A activity with products in accordance with the invention exhibiting a purely UV-B activity.

These new s-triazine compounds can thus be used as sunscreen agents for the human skin and for the hair. They can also be used as light-protective agents in the plastics industry.

In the above formulae (1) to (5), the alkyl radicals can be linear or branched and selected in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexy) and tert-octyl radicals. The preferred alkyl radicals R according to the invention are methyl, ethyl, propyl, n-butyl, n-octyl and 2-ethylhexyl radicals. More preferably still, the R radicals are all methyl radicals.

It is preferable, among the compounds of formula (I) above, to employ those in which the W radical corresponds to the formula (3) or to the formula (4), i.e., those in which the silicone radical is a linear diorganosiloxane radical.

Preference is more particularly given, among the linear diorganosiloxane radicals coming within the scope of the present invention, to random or well defined block derivatives exhibiting at least one, and more preferably still all, of the following characteristics:

R is alkyl and more preferably still is methyl, r is from 0 to 3 inclusive: s is from 0 to 3 inclusive.

Another subject of the present invention is the process for the preparation of the compounds of formula (I).

The compounds of formula (I) can be obtained according to the reaction scheme below:

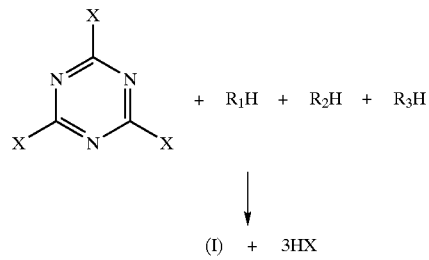

where $R_1$, $R_2$ and $R_3$ correspond to the above definitions and X represents a halogen, in particular chlorine or bromine.

The operations of grafting the various above radicals $R_1$, $R_2$ and $R_3$ onto the s-triazine can be carried out independently of one another and in any order. Preferably, the group or groups corresponding to the —NH—F radicals are first grafted onto the s-triazine and then the —NH—Z—W group or groups corresponding to the aminosilicone chains are subsequently grafted onto the s-triazine.

The above reactions can optionally be carried out in the presence-of a solvent, such as, for example, toluene, xylene or alternatively an acetone/water mixture.

The above reactions can also optionally be carried out in the presence of a base, such as sodium hydroxide, carbonates or alternatively an amine.

The R₁H or R₃H compounds corresponding to the —NH—F radicals can be prepared according to known methods.

Thus, the preparation of the amino derivatives of benzylidenecamphor is described in the document "Haller, Boudin, Annales de Chimie, 9th series, volume XVII (1922)". Mention may be made, as amino derivative of benzylidenecamphor which is particularly well suited to the preparation of the compounds according to the invention, of 4-aminobenzylidenecamphor.

The preparation of the amino derivatives of benzalmalonate is described, for example, in GB 1,064,116. Mention may be made, as amino derivatives of benzalmalonate which are particularly well suited to the preparation of the compounds of the invention, of dimethyl 4-aminobenzalmalonate, diethyl 4-aminobenzalmalonate, diisopropyl 4-amino-benzalmalonate or alternatively diisobutyl 4-amino-benzalmalonate.

The preparation of the amino derivatives of benzoic acid is described in particular in FR 2,151,503. Mention may be made, as amino derivatives of benzoic acid which are particularly well suited to the preparation of the compounds according to the invention, of ethyl 4-aminobenzoate and butyl 4-aminobenzoate.

The preparation of the amino derivatives of benzotriazole is described, for example, in FR 1,324,897 or alternatively in the article by T. Konstantinova et al., Polymer Degradation and Stability, 43, 187 (1994). Mention may in particular be made, as amino derivatives of benzotriazole which are particularly well suited to the preparation of the compounds according to the invention, of 2-(2-hydroxy-5-aminophenyl)-5-methoxybenzotriazole described in EP 221,630, 2-(2-hydroxy-4-aminophenyl)benzotriazole described in U.S. Pat. No. 3,159,646, 2-(2-hydroxyphenyl)-5-aminobenzotriazole described in U.S. Pat. No. 3,159,646 and GB 1,346,764, 2-(2-hydroxy-5-methylphenyl)-5-aminobenzotriazole described in U.S. Pat. No. 3,159,646, 2-(2-hydroxy-5-aminophenyl)benzotriazole described in the article by J. Belusa et al., Chem. Zvesti, 2-(2-hydroxy-5-aminophenyl)-5-chlorobenzotriazole described in the article by H. S. Freeman et al., Dyes and Pigments, 20, 171, (1992), 2-(2-hydroxy-4-aminophenyl)-5-chlorobenzotriazole described in the article by H. S. Freeman et al., Dyes and Pigments, 20, 171 (1992), 2-(2-hydroxy-3-amino-5-methylphenyl)benzotriazole described in DE 2,128,005 and GB 1,346,764, and 2-(2-hydroxy-3-amino-5-t-butylphenyl) benzotriazole described in DE 2,128,005 and GB 1,346,764.

The preparation of the amino derivatives of benzoxazole is described in particular in U.S. Pat. No. 2,334,348. Mention may in particular be made, as amino derivatives of benzoxazole which are particularly well suited to the preparation of the compounds of the invention, of 2-phenyl-5-aminobenzoxazole.

The preparation of the amino derivatives of benzothiazole is also described, for example, in U.S. Pat. No. 2,334,348. Mention may in particular be made, as amino derivatives of benzothiazole which are particularly well suited to the preparation of the compounds of the invention, of 2-(para-aminophenyl)-6-methylbenzothiazole.

The preparation of the amino derivatives of salicylic acid is described in particular in FR 2,385,685. Mention may be made, as amino derivatives of salicylic acid which are particularly well suited to the preparation of the compounds according to the invention, of ethyl 4-aminosalicylate or alternatively isobutyl 4-aminosalicylate or alternatively ethyl 5-aminosalicylate.

Mention may be made, as amino derivative of cinnamic acid, of, for example, ethyl 4-aminocinnamate.

The preparation of the amino derivatives of cyanoacrylate is described, for example, in the article J. Soc. Dyers Color. (1977), 93, p. 126–133. Mention may be made, as amino derivatives of cyanoacrylate which are particularly well suited to the preparation of the compounds of the present invention, of ethyl α-cyano-4-aminocinnamate, isopropyl α-cyano-4-aminocinnamate or alternatively 2-ethylhexyl α-cyano-4-aminocinnamate.

The R₂H and R₃H compounds corresponding to the aminosilicone chains (—NH—Z—W radicals) can also be prepared according to known processes.

The preparation of aminosiloxanes is described, for example, in GB 2,185,984. Mention may be made, as aminosiloxanes which are particularly well suited to the preparation of the compounds according to the invention, of aminopropylheptamethyltrisiloxane, aminoisobutylheptamethyltrisiloxane or alternatively trimethylsilylaminodimethicones, such as: the product sold under the trade name "X₂-8260" by the company Dow Corning, amine number 2.8 meq/gram; the product sold under the trade name "SLM 55051/3" by the company Wacker, amine number 0.47 meq/gram; dimethyl(C₁₂ alkyl) PDMSs, such as the product sold under the trade name "SLM 23046/1" by the company Wacker, amine number 1.2 meq/gram; α,ω-trimethylated polymethyl(fatty) alkylarylalkylsiloxanes, such as the product sold under the trade name "SLM 23056/2" by the company Wacker, amine number 1.3 meq/gram; or PDMSs in which the NH₂ radical is in the α and ω position on an alkyl site, such as the products sold under the trade name "Tegomer A-SI 2120", amine number 1.95 meq/gram, and "Tegomer A-SI 2320", amine number 0.86 meq/gram, by the company Goldschmidt.

The preparation of cyclic aminosiloxanes is described, for example, in the article by A. Kopylov, Zh. Obshch. Khim., 54(2), 367–71 (1984).

The preparation of aminosilanes is described, for example, in EP 321,174.

Mention may be made, as aminosilane derivatives which are particularly well suited to the preparation of the compounds of the present invention, of aminopropyltrimethylsilane and aminopropyltriethylsilane.

Another subject of the present invention is a composition comprising a compound of formula (I) according to the invention in an appropriate vehicle. The vehicle can be, for example, a plastic composition. It can also be appropriate for topical application. In this case, the composition according to the invention is a cosmetic composition which comprises a cosmetically acceptable vehicle.

The composition according to the invention is preferably a composition intended to protect a material sensitive to ultraviolet radiation, in particular to sunlight, comprising an effective amount of at least one compound in accordance with the invention. In a preferred embodiment of the invention, this composition is intended to protect the skin and/or the hair.

The compounds of formula (I) are generally present in the composition of the invention in proportions of from 0.1% to 20% by weight, preferably from 0.5% to 10% by weight, with respect to the total weight of the composition.

The compositions according to the invention can, of course, contain one or more additional hydrophilic or lipophilic sunscreen agents which are active in the UV-A and/or UV-B (absorbers), other than the compounds in accordance with the present invention. These additional screening agents can in particular be selected from cinnamic derivatives, salicylic derivatives, camphor derivatives, triazine derivatives, benzophenone derivatives, dibenzoylmethane derivatives, β,β-diphenylacrylate derivatives, derivatives of p-aminobenzoic acid, or the screening polymers and screening silicones described in PCT Application WO-93/04665. Other examples of organic screening agents are given in European Patent Application EP-A 0,487,404.

The compositions according to the invention can also contain agents for the artificial tanning and/or browning of the skin (self-tanning agents), such as, for example, dihydroxyacetone (DHA).

The compositions according to the invention can also contain pigments or alternatively nanopigments (mean size of the primary particles: generally from 5 nm to 100 nm, preferably from 10 nm to 50 nm) of coated or uncoated metal oxides, such as, for example, nanopigments of titanium oxide (amorphous or crystallized in the rutile and/or anatase form), of iron oxide, of zinc oxide, of zirconium oxide or of cerium oxide, which are all UV-photoprotective agents well known per se. Moreover, alumina and/or aluminum stearate are conventional coating agents. Such coated or uncoated metal oxide nanopigments are described in particular in European Patent Applications EP-A-0,518,772 and EP-A-0,518,773.

It can contain the cosmetic adjuvants commonly used in the cosmetics field, such as fatty substances, organic solvents, silicones, thickeners, softeners, additional sunscreen agents, antifoaming agents, moisturizing agents, fragrances, preservatives, surfactants, fillers, sequestering agents, anionic, cationic, non-ionic or amphoteric polymers or their mixtures, propellants, basifying or acidifying agents, dyes, pigments or nanopigments, in particular those intended to provide an additional photoprotective effect by physical blocking of ultraviolet radiation, or any other ingredient commonly used in cosmetics, in particular for the manufacture of anti-sun compositions.

Mention may be made, among organic solvents, of lower alcohols and polyols, such as ethanol, isopropanol, propylene glycol, glycerol and sorbitol.

The fatty substances can be composed of an oil or of a wax or their mixtures, fatty acids, fatty acid esters, fatty alcohols, petrolatum, paraffin, lanolin, hydrogenated lanolin or acetylated lanolin. The oils can be selected from animal, vegetable, mineral or synthetic oils and in particular hydrogenated palm oil, hydrogenated castor oil, liquid petrolatum, liquid paraffin, Purcellin oil, volatile or non-volatile silicone oils, and isoparaffins.

Of course, a person skilled in the art will take care to choose the optional additional compound or compounds mentioned above and/or their amounts so that the advantageous properties intrinsically attached to the compound in accordance with the invention are not, or not substantially, detrimentally affected by the envisaged addition or additions.

The cosmetic composition of the invention can be used as a composition for protecting the human epidermis or the hair against ultraviolet rays, as an anti-sun composition or as a make-up product.

This composition can be provided in particular in the form of a lotion, of a thickened lotion, of a gel, of a cream, of a milk, of a powder or of a solid stick and can optionally be packaged as an aerosol and be provided in the form of a foam or of a spray.

When the cosmetic composition according to the invention is more particularly intended for the protection of the human epidermis against UV rays or as an anti-sun composition, it can be provided in the form of a suspension or of a dispersion in solvents or fatty substances or alternatively in the form of an emulsion (in particular of O/W or W/O type but preferably O/W), such as a cream or a milk, or of a vesicular dispersion, or in the form of an ointment, of a gel, of a solid stick or of an aerosol foam. The emulsions can additionally contain anionic, non-ionic, cationic or amphoteric surface-active agents.

When the cosmetic composition according to the invention is used for the protection of the hair, it can be provided in the form of a shampoo, of a lotion, of a gel or of a composition to be rinsed out, to be applied before or after shampooing, before or after dyeing or bleaching, or before, during or after a permanent-waving or hair-straightening operation, of a styling or treating lotion or gel, of a lotion or gel for blow-drying or hair setting, of a hair lacquer, or of a composition for the permanent waving, straightening, dyeing or bleaching of the hair.

When the cosmetic composition according to the invention is used as a product for making up the eyelashes, eyebrows, skin or hair, such as a cream for treatment of the epidermis, a foundation, a lipstick, an eye shadow, a blusher, an eyeliner, a mascara or a coloring mousse, it can be provided in the anhydrous or aqueous, solid or pasty form, such as oil-in-water or water-in-oil emulsions, suspensions or alternatively gels.

A further subject of the invention is the use of a compound in accordance with the invention in, or for the manufacture of, compositions intended to protect materials sensitive to ultraviolet radiation, in particular to sunlight.

A further subject of the invention is the use of a compound of general formula (I) in accordance with the invention for the preparation of a medicament intended to prevent the harmful effects of UV radiation.

A further subject of the invention is the use of a compound of general formula (I) in accordance with the invention as agent for screening UV radiation, in particular for controlling the color of the skin.

A final subject of the invention is a non-therapeutic process for protecting the skin and/or the hair against ultraviolet radiation, in particular sunlight, which consists in applying, to the skin or to the hair, an effective amount of the cosmetic composition defined above or of a compound of formula (I) as defined above.

Finally, a subject of the invention is a non-therapeutic process for controlling the variation in color of the skin due to UV radiation, which consists in applying, to the skin, an effective amount of the cosmetic composition defined above or of a compound of formula (I) as defined above.

The following examples illustrate the invention without, however, limiting the scope thereof.

EXAMPLE 1

Preparation of 2-(butyl 4'-ylaminobenzoate)-4,6-bis{[1,3,3,3-tetramethyl-1-[(trimethylsilyl)oxy]disiloxanyl]propyl-3-ylamino}-s-triazine 1st Stage: preparation of 2-(butyl 4'-ylaminobenzoate)-4,6-dichloro-s-triazine Butyl 4-aminobenzoate (19.32 g, 0.1 mol), in solution in 200 ml of acetone, was added dropwise, at 0–5° C., to a solution of cyanuric chloride (18.4 g, 0.1 mol) in 100 ml of acetone/50 ml of water, followed by 100 ml of 0.1N sodium bicarbonate, over 1 hour. Stirring was maintained for 1 hour. After filtering off the precipitate, washing with water and drying, 2-(butyl 4'-ylaminobenzoate)-4,6-dichloro-s-triazine (33 g, yield=96%) was obtained, which product had the following characteristics:

white powder
M.p.: 248° C.
UV (95% Ethanol) $\lambda_{max}$=294 nm, $\epsilon_{max}$=28,960
Elemental analysis for $C_{14}H_{14}Cl_2N_4O_2$:
Calculated: C,49.28; H,4.14; Cl,20.78; N,16.42; O,9.38.
Found: C,49.32; H,4.18; Cl,20.94; N,16.44; O,9.61.

2nd Stage: preparation of the compound of Example 1

The preceding derivative (0.2 g, 5.86×10$^{-4}$ mol) and 1-amino-3-[1,3,3,3-tetramethyl-1-[(trimethylsilyl)oxy]disiloxanyl]propane (0.8 g, 28.7×10$^{-4}$ mol) were heated at 90° C. for 2 hours under nitrogen. The reaction mixture was chromatographed on silica (eluent: 70/30 heptane/ethyl acetate). 0.34 g (Yield: 70%) of the derivative of Example 1 was obtained in the form of a colorless oil:

UV (Ethanol) $\lambda_{max}$=300 nm, $\epsilon_{max}$=40,800
Elemental analysis for $C_{34}H_{70}N_5O_6Si_6$
Calculated: C, 49.35; H, 8.53; N, 10.16; Si, 20.36.
Found: C, 48.95; H, 8.39; N, 10.05; Si, 20.28.

EXAMPLE 2

Preparation of 2,4-bis(4'-ylamnobenzylidenecamphor)-6-{[1,3,3,3-tetramethyl-1-[(trimethylsilyl)oxy]disiloxanyl]propyl-3-ylamino}-s-triazine 1st Stage: preparation of 2,4-bis(4'-ylaminobenzylidenecmphor)-6-chloro-s-triazine 4-Aminobenzylidenecamphor (12.76 g, 0.05 mol), in solution in 75 ml of acetone, was added dropwise, at 35–40° C., to a solution of cyanuric chloride (4.61 g, 0.025 mol) in 50 ml of acetone, followed by 50 ml of N sodium hydroxide, over 2 hours. Stirring was maintained for 1.5 hours. After filtering off the precipitate, washing with water and drying, 2,4-bis(4'-ylaminobenzylidenecamphor)-6-chloro-s-triazine (12.6 g, yield=81%) was obtained, which product had the following characteristics:

pale-yellow powder
M.p.: 255° C.
UV (95% Ethanol) $\lambda_{max}$=346 nm, $\epsilon_{max}$=61,900
Elemental analysis for $C_{37}H_{40}ClN_5O_2$
Calculated: C:71.42; H:6.48; Cl:5.70; N:11.26; O:5.14.
Found: C:71.43; H:6.51; Cl:5.66; N:11.15; O:5.35.

2nd Stage: preparation of the compound of Example 2

The preceding derivative (0.075 g, 1.2×10$^{-4}$ mol) and 1-amino-3-[1,3,3,3-tetramethyl-1-[(trimethylsilyl)oxy]disiloxanyl]propane (0.375 g, 13.4×10$^{-4}$ mol) were heated at 90° C. for 1 hour under nitrogen. The reaction mixture was chromatographed on silica (eluent: 70/30 heptane/ethyl acetate). 0.07 g (Yield: 70%) of the derivative of Example 2 was obtained, which derivative had the following characteristics:

pale-yellow powder
M.p.: 107° C.
UV (Ethanol) $\lambda_{max}$=354 nm, $\epsilon_{max}$=66,460
Elemental analysis for: $C_{47}H_{68}N_6O_4Si_3$
Calculated: C:65.24; H:7.92; N:9.71; Si:9.74.
Found: C:64.98; H:8.00; N:9.49; Si:9.46.

EXAMPLE 3

Preparation of 2,4-bis(butyl 4'-ylaminobenzoate)-6-{[1,3,3,3-tetramethyl-1-[(trimethylsilyl)oxy]disiloxanyl]propyl-3-ylamino}-s-triazine 1st Stage: preparation of 2,4-bis(butyl 4'-ylaminobenzoate)-6-chloro-s-triazine Butyl aminobenzoate (9.94 g, 0.0515 mol), in solution in 15 ml of dioxane, was added dropwise to a solution of cyanuric chloride (9.2 g, 0.05 mol) in 100 ml of dioxane, followed by 3.5 g of potassium carbonate in solution in 15 ml of water. The reaction mixture was then brought to 40° C. and 9.94 g of butyl aminobenzoate, in solution in 15 ml of dioxane, followed by 3.5 g of potassium carbonate, were again introduced. Stirring was then maintained for 3 hours at 65° C. The reaction mixture was filtered. 250 ml of water were added to the filtrate. The precipitate formed was filtered off, dried and recrystallized from 250 ml of toluene. 16.5 g (Yield: 66%) of the expected derivative were obtained in the form of a white powder.

2nd Stage: preparation of the compound of Example 3

The preceding derivative (13.7 g, 0.0275 mol) and 1-amino-3-[1,3,3,3-tetramethyl-1-[(trimethylsilyl)oxy]disiloxanyl]propane (19.53 g, 0.075 mol), in 20 ml of toluene, were brought to reflux for 3 hours. After concentrating, the reaction mixture was chromatographed on silica (eluent: 60/40 heptanelethyl acetate). 16 g (Yield: 78%) of the derivative of Example 3 were obtained, which derivative had the following characteristics:

white powder
M.p.: 110° C.
UV (95% Ethanol) $\lambda_{max}$=310 nm, $\epsilon_{max}$=75,510
Elemental analysis for $C_{35}H_{56}N_6O_6Si_3$
Calculated: C:56.72; H:7.62; N:11.34; Si:11.37.
Found: C:56.42; H:7.65; N:11.38; Si:11.70.

EXAMPLE 4

Preparation of 2-(2-benzotriazol-2-yl-4-methyl-6-ylaminophenol)-4,6-bis{[1,3,3,3-tetramethyl-1-[(trimethylsilyl)oxy]disiloxanyl]propyl-3-ylamino}-s-triazine 1st Stage: preparation of 2-(2-benzotriazol-2-yl-4-methyl-6-ylaminophenol)-4,6-dichloro-s-triazine The following were added to a solution of cyanuric chloride (1.46 g, 0.0079 mol) in 20 ml of acetone: 10 ml of water, then, at 0–5° C. and dropwise, 2-benzotriazol-2-yl-4-methyl-6-aminophenol (1.9 g, 0.0079 mol) in solution in 100 ml of dioxane, and then 0.66 g (0.0079 mol) of sodium bicarbonate in solution in 20 ml of water. Stirring was maintained for 2 hours; 250 ml of water were added. After filtering off the precipitate, washing with water and drying, 2-(2-benzotriazol-2-yl-4-methyl-6-ylaminophenol)-4,6-dichloro-s-triazine was obtained (3 g, yield: 100%), which product had the following characteristics:

pale-yellow powder
M.p.: 221–222° C.

2nd Stage: preparation of the compound of Example 4

The preceding derivative (1.55 g, 0.004 mol) and 1-amino-3-[1,3,3,3-tetramethyl-1-[(trimethylsilyi)oxy]disiloxanyl]propane (6 g, 0.021 mol) were heated at 90° C. for 2 hours under nitrogen. The reaction mixture was chromatographed on silica (eluent: 50/50 heptane/dichloromethane). 2.8 g (Yield: 80%) of the derivative of Example 4 were obtained, which derivative had the following characteristics:

pale-yellow powder
M.p.: 101–102° C.
UV (Ethanol) $\lambda_{max}$=324 nm, $\epsilon_{max}$=22,000

Elemental analysis for $C_{36}H_{67}N_9O_5Si_6$
Calculated: C 49.45; H 7.72; N 14.41; Si 19.27.
Found: C 49.52; H 7.71; N 14.21; Si 19.23.

EXAMPLE 5

Preparation of 2,4-bis(diisobutyl 4'-ylaminobenzalmalonate)-6-{[1,1,1,3-tetramethyl-1-[(trimethylsilyl)oxy]disiloxanyl]propyl-3-ylamino}-s-triazine 1st Stage: preparation of 2,4-dichloro-6-{[1,1,3,3-tetramethyl-1-[(trimethylsilyl)oxy]disiloxanyl]propyl-3-ylamino}-s-triazine A solution of cyanuric chloride (1.84 g, 0.01 mol) in 20 ml of acetone had added to it, at 0° C. and dropwise, 1-amino-3-{[1,1,3,3-tetramethyl-1-[(trimethylsilyl)oxy]disiloxanyl]propane (2.79 g, 0.01 mol) and a solution of sodium bicarbonate (0.84 g, 0.01 mol) in 12 ml of water, so that the pH was from 3 to 5. At the end of introduction, the pH was 3. Stirring was maintained for 1 hour at 10° C. and then the temperature was allowed to rise to laboratory temperature. The reaction mixture was filtered. The precipitate formed was filtered off, washed with water, superficially dried and thoroughly dried; 3.4 g of the expected product were obtained in the form of a white powder (yield: 80% and M.p.: 59° C.).

2nd Stage: preparation of the compound of Example 6

The preceding derivative (1.1 g, 0.0023 mol) and the diisobutyl para-aminobenzalmalonate (3.19 g, 0.01 mol) were heated at 90–100° C. for 1 hour 30 minutes in 30 ml of toluene. After concentrating, the reaction mixture was chromatographed on silica (eluent: 98/2 dichloromethane/methanol). 1.5 g (Yield: 65%) of the derivative of Example 6 were obtained, which derivative had the following characteristics:

transparent wax
UV (Ethanol) $\lambda_{max}$=356.5 nm, $\epsilon_{max}$=65,650
Elemental analysis for $C_{49}H_{76}N_6O_{10}Si_3$
Calculated: C: 59.24; H: 7.71; N: 8.46; Si: 8.48.
Found: C: 59.13; H: 7.70; N: 8.34; Si: 8.50.

EXAMPLE 6

A concrete example is given here of a cosmetic composition in accordance with the invention, namely an O/W anti-sun emulsion:

| | |
|---|---|
| compound of Example 3 | 5% |
| 80/20 mixture of cetylstearyl alcohol and of oxyethylenated (33 EO) cetylstearyl alcohol, sold under the trade name "Dehsconet 390" by Tensia | 7% |
| mixture of glycerol mono- and distearate, sold under the trade name "Cerasynth SD" by the company ISP | 2% |
| cetyl alcohol | 1.5% |
| polydimethylsiloxane, sold under the trade name "DC200 Fluid" by the company Dow Corning | 1.5% |
| benzoate of $C_{12}$–$C_{15}$ alcohols, sold under the trade name "Finsolv TN" by the company Finetex | 15% |
| glycerol | 20% |
| preservatives | q.s. |
| demineralized water | q.s. for 100% |

This O/W anti-sun emulsion was prepared according to conventional techniques for the preparation of emulsions, by dissolving the screening agent in the fatty phase containing the emulsifiers, by heating this fatty phase to approximately 70–80° C. and by adding, with Vigorous stirring, the water heated to the same temperature. Stirring was maintained for 10 to 15 minutes, the mixture was then allowed to cool with moderate stirring, and the preservatives were finally added at approximately 40° C.

An anti-sun cream was thus obtained which was particularly effective against UV-B radiation.

We claim:
1. A compound of the formula (I):

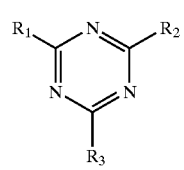

(I)

in which:

$R_1$ represents an —NH—F radical, $R_2$ represents an —NH—Z—W radical, $R_3$ is $R_1$, $R_2$, an $NHR_8$ radical or an $N(R_8)_2$ radical, with $R_8$ being a linear or branched $C_1$–$C_{20}$ alkyl radical, F represents a screening chromophore chosen from derivatives of benzylidenecamphor, of benzalmalonate, of benzoate, of benzotriazole, of benzimidazole, of benzoxazole, of benzothiazole, of salicylate, of cinnamate, and of cinnamonitrile, Z represents a divalent radical providing the connection between —NH— an, —W, W represents either a silicone radical comprising at least one unit of formula (1):

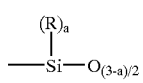

(1)

in which R denotes a saturated or unsaturated $C_1$–$C_{30}$ hydrocarbon group, a halogenated $C_1$–$C_8$ hydrocarbon group or a trimethylsilyloxy group and a is 1 or 2, or a radical of formula (2):

(2)

in which $R'_1$, $R'_2$ and $R'_3$, which are identical or different, are linear or branched $C_1$–$C_8$ alkyl or alkenyl radicals.

2. A compound according to claim 1, wherein said chromophore F is selected independently from the radicals of formulae A to E:

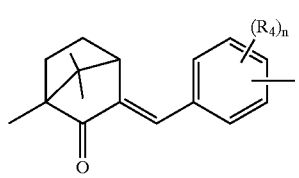

A

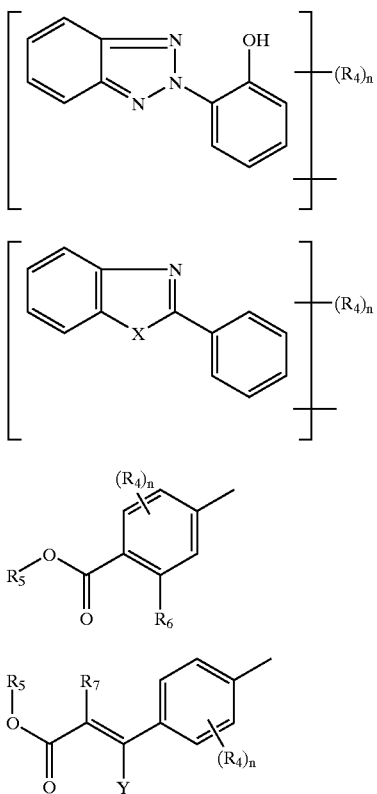

in which:
- $R_4$, which are identical or different, denote a linear or branched $C_1$–$C_8$ alkyl radical or a $C_1$–$C_4$ alkoxy radical, it being possible for two adjacent $R_4$ groups on the same aromatic nucleus together to form an alkylidenedioxy group in which the alkylidene group contains 1 or 2 carbon atoms,
- n is 0, 1 or 2,
- $R_5$ is a linear or branched $C_1$–$C_{20}$ alkyl radical,
- $R_6$ represents a hydrogen atom, a hydroxyl radical or a $C_1$–$C_6$ alkoxy radical,
- $R_7$ represents a hydrogen atom, $COOR_5$ or a cyano radical,
- X is an oxygen or sulphur atom or an N—$R_9$ group, with $R_9$ being a hydrogen atom or a linear or branched $C_1$–$C_4$ alkyl radical, and
- Y represents a hydrogen atom or a phenyl radical optionally substituted by a $C_1$–$C_4$ alkyl or alkoxy radical.

3. A compound according to claim 1, wherein said divalent radical Z is a radical of the formula (a) or (b):

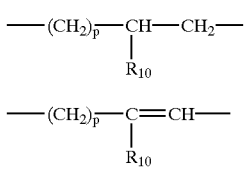

in which $R_{10}$ represents a hydrogen atom or a saturated or unsaturated, linear or branched $C_1$–$C_8$ alkyl radical and p is an integer from 0 to 10.

4. A compound according to claim 3, wherein W is a silicone radical of one of the formulae (3) to (5):

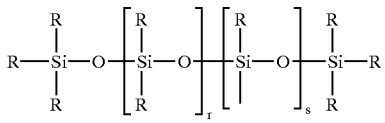

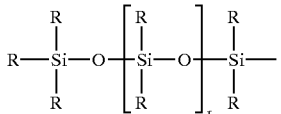

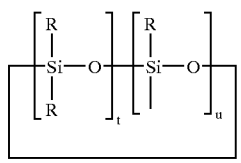

in which:
- R, which are identical or different, are saturated or unsaturated, linear or branched $C_1$–$C_{10}$ alkyl radicals, a phenyl radical or a 3,3,3-trifluoropropyl radical, at least 80% by number of the R radicals being the methyl radical,
- r is an integer from 0 to 50 inclusive,
- s is an integer from 0 to 20 inclusive,
- u is an integer of from 1 to 6 inclusive,
- t is an integer from 0 to 10 inclusive, and
- t+u is equal to or greater than 3.

5. A compound according to claim 4, wherein W has the formula (4) or the formula (5).

6. A compound according to claim 1, wherein said compound of the formula (I) is 2-(butyl 4'-ylaminobenzoate)-4,6-bis{[1,3,3,3-tetramethyl-1-[(trimethylsilyl)oxy]disiloxanyl]propyl-3-ylamino}-s-triazine, 2,4-bis(4'-ylaminobenzylidenecamphor)-6-{[1,3,3,3-tetramethyl-1-[(trimethylsilyl)oxy]disiloxanyl]propyl-3-ylamino}-s-triazine, 2,4-bis(butyl 4'-ylaminobenzoate)-6-{[1,3,3,3-tetramethyl-1-[(trimethylsilyl)oxy]disiloxanyl]propyl-3-ylamino}-s-triazine, or 2-(2-benzotriazol-2-yl-4-methyl-6-ylaminophenol)-4,6-bis{[1,3,3,3-tetramethyl-1-[(trimethylsilyl)oxy]disiloxanyl]propyl-3-ylamino}-s-triazine.

7. A process for the preparation of a compound of the formula (I)

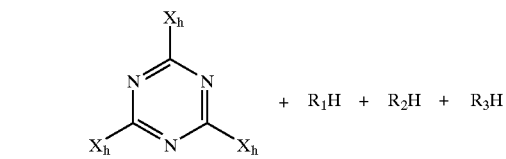

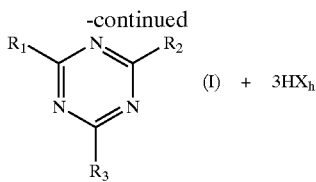

as defined in claim 1, said process comprising the following reaction scheme:
where $R_1$, $R_2$ and $R_3$ correspond to the definitions recited in claim 1 and $X_h$ represents a halogen.

8. A process according to claim 7, wherein $X_h$ represents chlorine or bromine.

9. A composition comprising a compound of formula (I) as defined in claim 1 in an appropriate vehicle.

10. A composition according to claim 9, wherein said composition is a plastic composition.

11. A composition accoriding to claim 9, wherein said composition is a cosmetic composition for protecting the skin and/or the hair from UV radiation, and wherein said vehicle is a cosmetically acceptable vehicle.

12. A composition according to claim 9, wherein said compound of formula (I) is present in the composition in an amount ranging from 0.1 to 20% by weight with respect to the total weight of the composition.

13. A composition according to claim 12, wherein said compound of formula (I) is present in the composition in an amount ranging from 0.5% to 10% by weight with respect to the total weight of the composition.

14. A process for the manufacture of a composition intended to protect materials sensitive to ultraviolet radiation, said process comprising including in said composition at least one compound of formula (I) as defined in claim 1.

15. A process for the preparation of a medicament intended to prevent the harmful effects of UV radiation, said process comprising including in said medicament at least one compound of formula (I) as defined in claim 1.

16. An agent for screening UV radiation comprising a compound of formula (I) as defined in claim 1.

17. A non-therapeutic process for protecting the skin and/or the hair against ultraviolet radiation comprising applying, to the skin or to the hair, an effective amount of a compound of formula (I) as defined in claim 1.

18. The process of claim 17, wherein said ultraviolet radiation is sunlight.

19. A non-therapeutic process for protecting the skin and/or the hair against ultraviolet radiation comprising applying, to the skin or to the hair, an effective amount of a composition comprising a compound of formula (I) as defined in claim 1, in an appropriate vehicle.

20. A non-therapeutic process for controlling the variation in color of the skin due to UV radiation, comprising applying to the skin an effective amount of a compound of formula (I) as defined in claim 1.

21. A non-therapeutic process for controlling the variation in color of the skin due to UV radiation, comprising applying to the skin an effective amount of a composition comprising a compound of formula (I) as defined in claim 1, in an appropriate vehicle.

* * * * *

UNITED STATES PATENT AND TRADEMARK OFFICE
CERTIFICATE OF CORRECTION

PATENT NO. : 6,517,742 B1
DATED : February 11, 2003
INVENTOR(S) : Hervé Richard et al.

It is certified that error appears in the above-identified patent and that said Letters Patent is hereby corrected as shown below:

Column 14,
Line 36, "an," should read -- and --; and

Column 17,
Line 19, "accoriding" should read -- according --.

Signed and Sealed this

Seventeenth Day of June, 2003

JAMES E. ROGAN
*Director of the United States Patent and Trademark Office*